(12) United States Patent
Takagi et al.

(10) Patent No.: US 6,676,638 B2
(45) Date of Patent: *Jan. 13, 2004

(54) INDWELLING NEEDLE WITH AN INNER NEEDLE RETRACTION MECHANISM

(75) Inventors: Hiroshi Takagi, Yokohama (JP); Kentaro Takemae, Kawasaki (JP); Kunihiko Tanaka, Akishima (JP)

(73) Assignees: Mitsubishi Pencil Kabushiki Kaisha, Tokyo (JP); Nipro Corporation, Osaka (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 126 days.

(21) Appl. No.: 09/779,173

(22) Filed: Feb. 8, 2001

(65) Prior Publication Data

US 2001/0016713 A1 Aug. 23, 2001

(30) Foreign Application Priority Data

Feb. 21, 2000 (JP) .......................................... 2000-43058

(51) Int. Cl.[7] .......................... A61M 5/178; A61M 5/00; A61M 5/32; A61M 25/00
(52) U.S. Cl. .................. 604/167.03; 604/192; 604/264; 604/164.08; 604/110; 604/198
(58) Field of Search .......................... 604/263, 164.01, 604/177, 110, 167.03, 264, 164.08, 198, 508, 167.04, 247, 192

(56) References Cited

U.S. PATENT DOCUMENTS

| | | | |
|---|---|---|---|
| 5,215,528 A | * | 6/1993 | Purdy et al. ........... 604/164.08 |
| 5,279,590 A | | 1/1994 | Sinko et al. |
| 5,520,654 A | * | 5/1996 | Wahlberg .................... 604/110 |
| 5,954,698 A | * | 9/1999 | Pike ...................... 604/167.03 |
| 5,993,470 A | | 11/1999 | Yoon |

FOREIGN PATENT DOCUMENTS

| | | | |
|---|---|---|---|
| JP | 06-086821 | 3/1994 | .......... A61M/25/00 |
| JP | 07-024071 | 1/1995 | .......... A61M/25/00 |
| JP | 09000629 | 1/1997 | ............ A61M/5/32 |
| JP | 09-000629 | 1/1997 | ............ A61M/5/32 |
| JP | 10-015074 | 1/1998 | .......... A61M/25/00 |

* cited by examiner

Primary Examiner—Brian L. Casler
Assistant Examiner—Roz Ghafoorian
(74) Attorney, Agent, or Firm—Darby & Darby

(57) ABSTRACT

An indwelling needle includes: a container barrel having a retraction mechanism (an actuator and urging element etc.,) for retracting the inner needle after use; and an outer needle support lid element for prohibiting the outer needle from being withdrawn into the container barrel. The outer needle support lid element has a gutter-like portion, which is a short cylinder formed in part with a cutout portion with its inside dimension designed so as to allow the inner needle to pass therethrough and be smaller than the outside dimension of the needle base (more exactly, the outer dimension of the flange of the needle base) of the outer needle.

2 Claims, 4 Drawing Sheets

INDWELLING NEEDLE WITH AN INNER NEEDLE RETRACTION MECHANISM

BACKGROUND OF THE INVENTION

1. Field of the Invention

The present invention relates to a technology of an indwelling needle comprised of a hard inner needle which punctures the skin and reaches the vein and a soft outer needle which is located outside of the inner needle and is indwelled within the vein and is directed to an indwelling needle with an inner needle retraction mechanism.

2. Description of the Prior Art

Various techniques have been proposed in order to prevent secondary infection.

For example, Japanese Patent Application Laid-Open Hei 9 No. 629 is directed to an 'indwelling needle' which aims at 'safety disposal of the inner needle of the used indwelling needle without any risk of the workers concerned being secondarily infected' and has a 'configuration which enables the inner needle to be fixed within the protection cover'.

Since a typical indwelling needle is comprised of a resin-made outer needle and a stainless inner needle, the risk of secondary infection due to 'needlestick injuries' arises from the inner needle. Therefore, other than that disclosed in Japanese Patent Application Laid-Open Hei 9 No. 629, there are several techniques of confining the inner needle, which would cause erroneous or accidental prick, within a tubular sleeve.

In general, the tubular sleeve keeps the inner needle therein and does not retract the outer needle. With regards to the mechanism for retraction, the mechanism preferably has a device for preventing the outer needle from being drawn into the tubular sleeve even if the mechanism malfunctions during and/or after the puncture of the inner and outer needles to the patient's skin. With this device, it is possible to secure necessary safety during the treatment and eliminate the burden on the patient due to doing over again. However, if the countermeasure against such a malfunction is attempted by devising inner needle retraction arrangements, a complex mechanism will be needed and also a troublesome operation for retraction of the inner needle will be needed.

Both the inner and outer needles are made to puncture the patient's skin and only the inner needle is pulled out while the outer needle remains therein. When the inner needle is pulled, in order to prevent the outer needle from being removed together with the inner needle, it is necessary to apply the finger around the contact area between the outer needle and the skin and/or the proximal part of the outer needle. In this case, if any projection is present around the proximal part of the outer needle, it is not desirable for 'the finger that is applied on the outer needle proximal part' because such a projection deteriorates fastness and readiness in handling.

SUMMARY OF THE INVENTION

It is therefore an object of the present invention to provide an indwelling needle with an inner needle retraction mechanism which is capable of retracting the inner needle, disallows the outer needle to be withdrawn by any malfunction and will not reduce fastness and readiness in handling.

It is another object of the present invention to provide an indwelling needle with an inner needle retraction mechanism which provides readiness in retracting the inner needle.

In order to achieve the above objects, the present invention is configured as follows:

The present invention is directed to an indwelling needle including a hard inner needle (12), a soft outer needle (11) and an inner needle retraction mechanism. That is, the present invention relates to an indwelling needle with an inner needle retraction mechanism, has a container barrel (1) having distal and proximal ends, and having an inner needle retraction mechanism (including an actuator 6 and urging element 8) for holding the inner needle (12) after use therein; and an outer needle support lid element (20) fixed at the distal end of the container barrel (1) for prohibiting the outer needle (11) from being withdrawn into the container barrel (1), and is characterized in that the outer needle support lid element (20) has a gutter-like portion, which is a short cylinder formed in part with a cutout portion (20C) and the inside dimension thereof is designed so as to allow the inner needle (12) to pass therethrough and be smaller than the outside dimension of the hub (11a) (more exactly, a flange 11b of hub 11a) of the outer needle (11).

In accordance with the above configuration of the present invention, the outer needle (11) together with the inner needle (12) is made to puncture the skin and reach the vein. Then, the inner needle (12) is withdrawn while the hub (11a) of the outer needle (11) being held. During this procedure, since the outer needle support lid (20) has the cutout portion (20c), the finger is able to hold the hub (11a) of the outer needle (11) without any obstruction. At this point, if the retraction mechanism (6 and 8) operates, the outer needle (11) will not be withdrawn into the container barrel (1) because there exists the outer needle support lid (20) having an inside dimension smaller than the outside dimension of the hub (11a) of the outer needle (11).

After the inner needle (12) is pulled out, an fluid injection tube for injection to the patient body such as an drip infusion tube is connected to the hub (11a) of the outer needle (11).

In the present invention, the inner needle retraction mechanism may be comprised of a guide groove (2) formed in the container barrel (1) in the longitudinal direction thereof, an actuator (6) fixed to the inner needle (12) and having an actuator piece (6a) for causing the inner needle (12) to be retracted into the container barrel (1) and an urging element (8) for urging the actuator (6) to the proximal side of the container barrel (1), and the cutout portion (20c) of the outer needle support lid element (20) may be positioned in proximity to the actuator piece (6a).

In this case, since the cutout portion (20c) of outer needle support lid element (20) is positioned in proximity to the actuator piece (6a), it is possible to perform the pulling action of the inner needle (12) while holding the hub (11a) of the outer needle (11) and the action of causing retraction of the inner needle (12) into the container barrel (1), without changing the grip of the container barrel (1).

DESCRIPTION OF THE PREFERRED EMBODIMENTS

Figure 1:
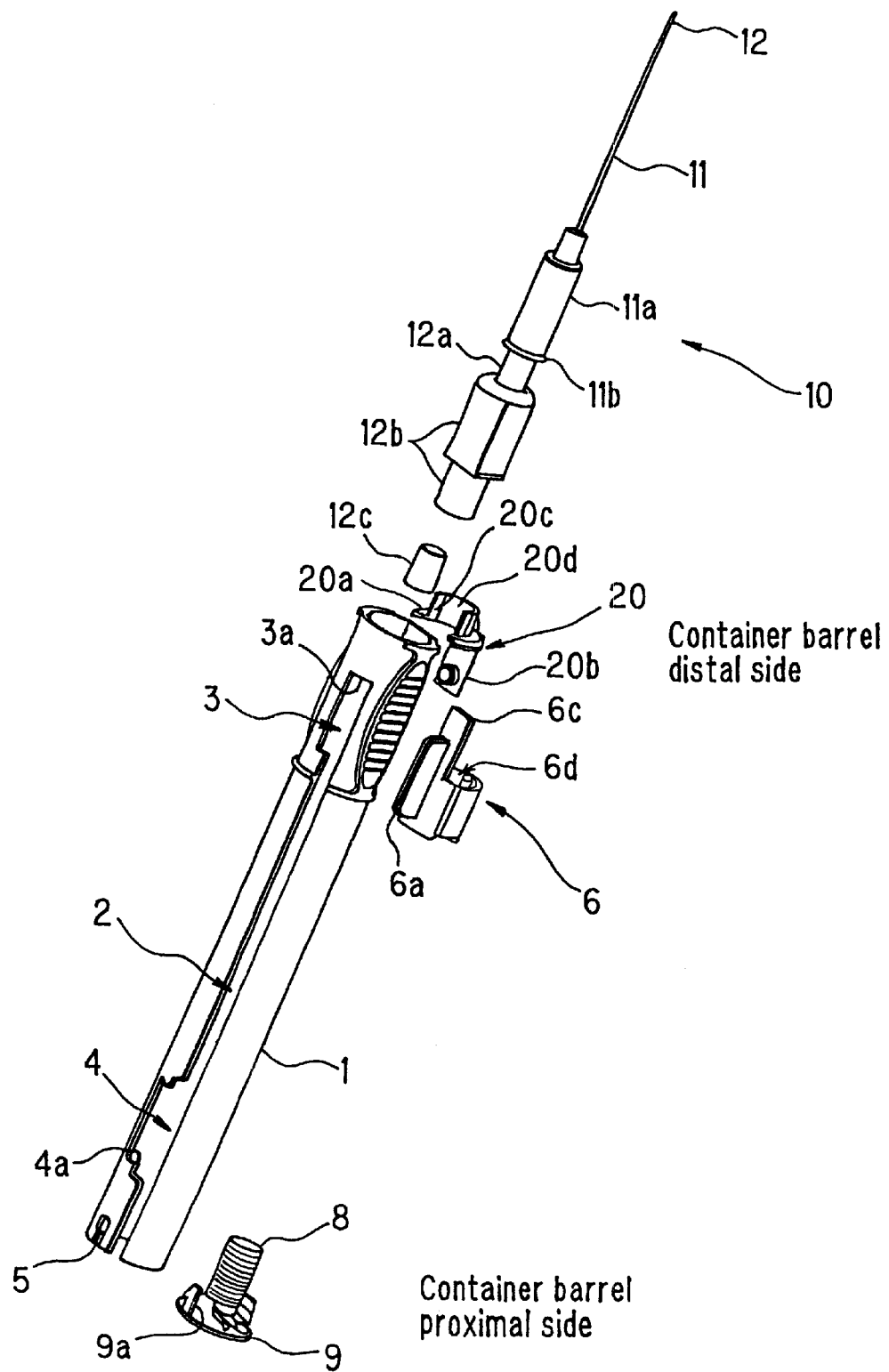
FIG. 1 is an exploded perspective view showing the embodiment of the present invention.
Figure 2:
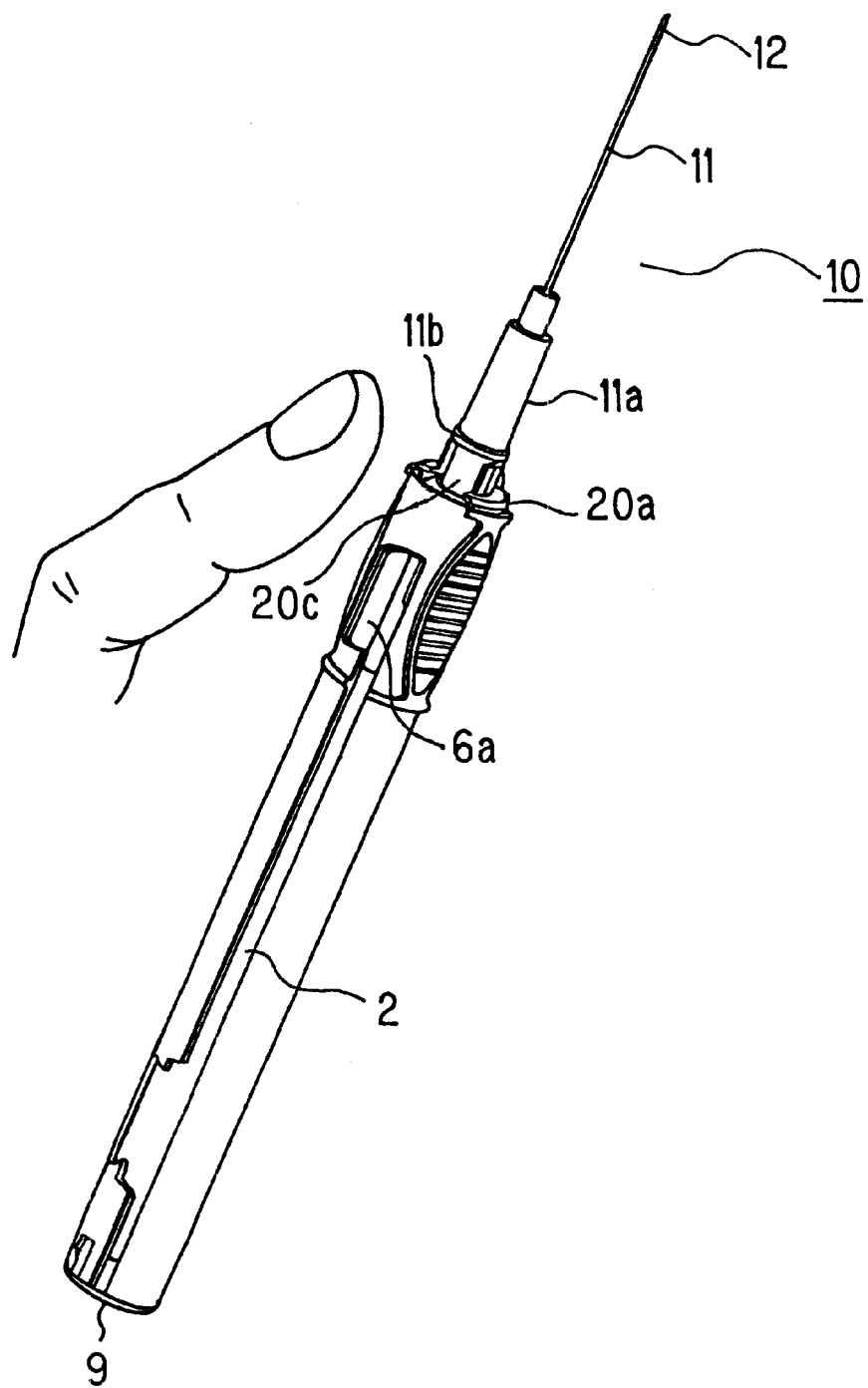
FIG. 2 is a perspective view showing the embodiment of the present invention in its use state.
Figure 3:
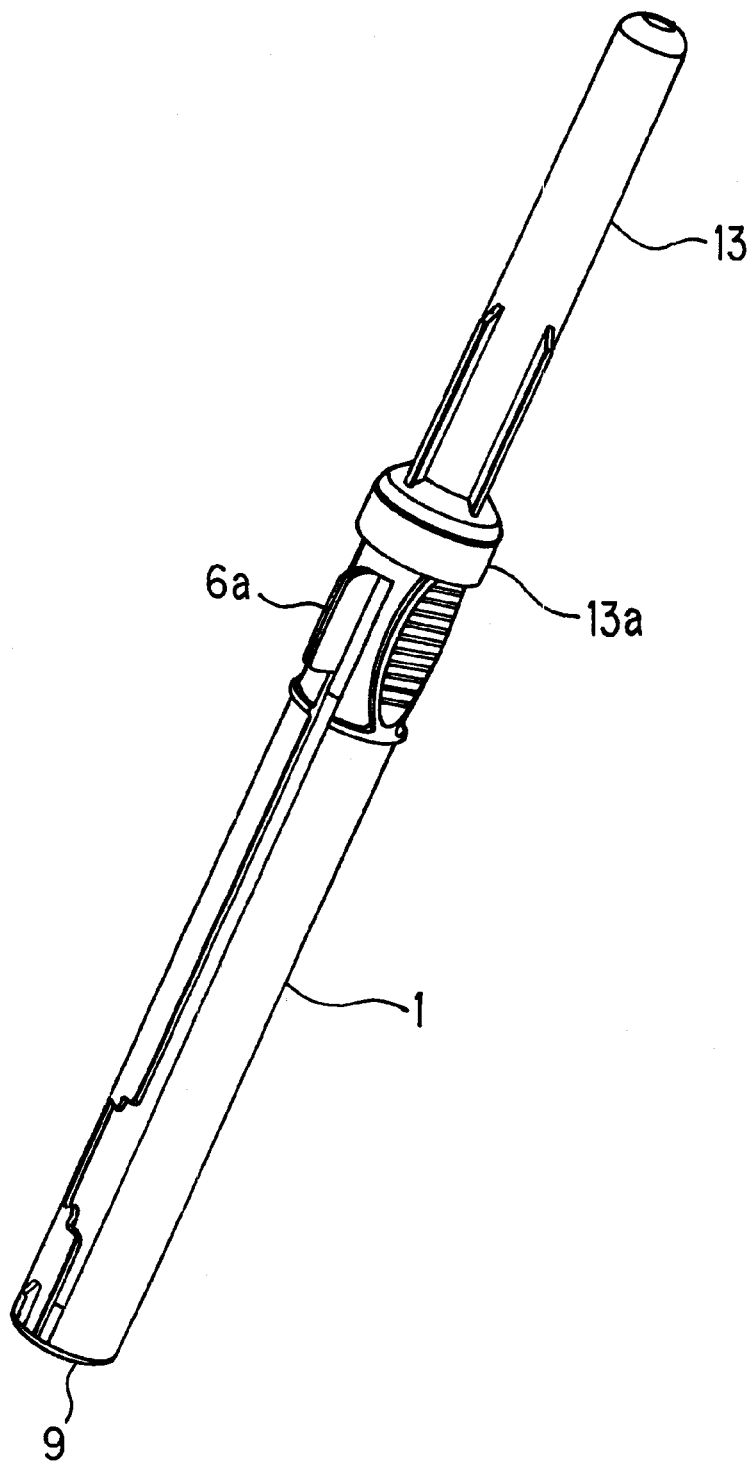
FIG. 3 is a perspective view showing the embodiment before use.
Figure 4:
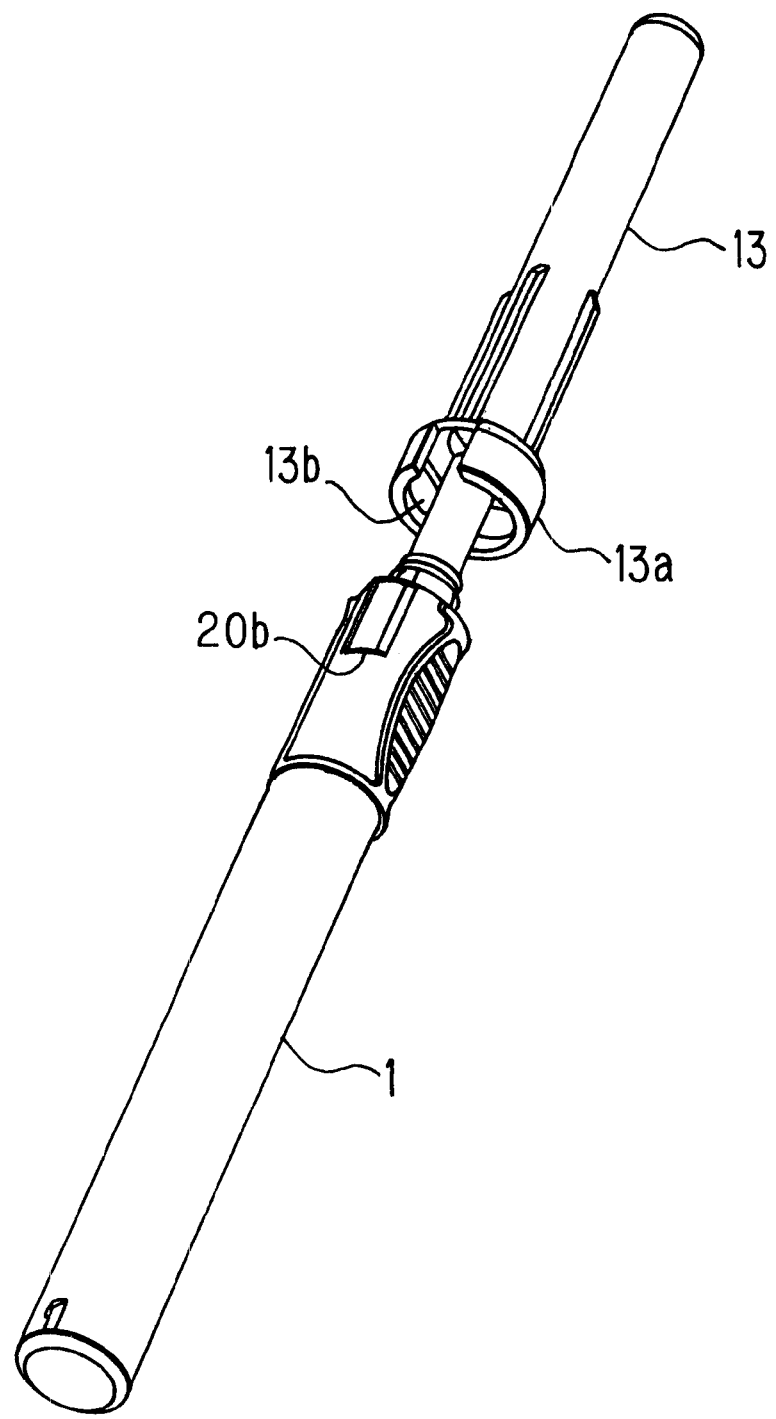
FIG. 4 is a perspective view showing the embodiment immediately before use.

The present invention will hereinafter be described in detail with reference to the embodiment and the accompanying drawings. The drawings used here include FIGS. 1 through 4. FIG. 1 is an exploded perspective view showing the embodiment of the present invention. FIG. 2 is a perspective view showing the embodiment of the present invention in its use state. FIG. 3 is a perspective view showing the embodiment before use. FIG. 4 is a perspective view showing the embodiment immediately before use.

Shown in FIG. 1 is an indwelling needle comprised of a hard inner needle 12 which punctures the skin and reaches the vein, a soft outer needle 11 which is located outside of inner needle 12 and is indwelled within the vein, and a container barrel 1 incorporating an inner needle retraction mechanism for retracting inner needle 12 after use.

The indwelling needle body, designated at 10, includes soft-resin made a hollow outer needle 11 which has a thin-walled distal part producing an increased contact with inner needle 12. This distal part is formed in hermetic contact with inner needle 12 so as not to easily come away. Provided at the proximal end of the outer needle is a hub 11a for connection with a medical tube such as drip infusion tube. A flange 11b is formed in hub 11a on its proximal side.

Inner needle 12 is of a hollow stainless steel needle, beveled at its tip forming a needle edge. On the proximal side of the inner needle, a cylindrical attachment part 12a inserted into hub 11a of outer needle 11 and a cylindrical joint part 12b coupled with an actuator 6 as a part of an aftermentioned retraction mechanism are continuously formed. A cylindrical resin-made filter 12c is stuffed at the end of joint part 12b. Here, inner needle 12 is not limited to hollow needles, but any hard type needle, e.g., a solid needle, may be used.

A container barrel 1 is a cylindrical sleeve for retracting inner needle 12 therein and incorporates the inner needle retraction mechanism and is long enough so that inner needle 12 can be retracted therein by the inner needle retraction mechanism. The inner needle retraction mechanism is comprised of a tail plug 9 fixed at the proximal end of container barrel 1, a coil spring 8 circumferentially fixed at its proximal end to the tail plug 9, an actuator 6 fixed to the distal end of coil spring 8 and also fixed to joint part 12b of inner needle 12.

Actuator 6 is positioned on the distal side of container barrel 1 and fixed therein until puncture of inner needle 12 and outer needle 11 to the patient is completed (to be referred to as 'during use' hereinbelow). In this state, coil spring 8 is stretched under loading. When inner needle 12 has been pulled out (to be referred to as 'after the use of inner needle 12'), actuator 6 is adapted to move toward the proximal end of container barrel 1 by the elastic force of coil spring 8. Next, the configuration of actuator 6 and container barrel 1 will be described in further detail.

Actuator 6 is comprised of a cylindrical attachment part 6d to which joint part 12b of inner needle 12 can be inserted and fixed, a plate-like rib 6c axially supporting joint part 12b of inner needle 12 fitted in attachment part 6d and a plate-like actuator piece 6a elongated in the axial direction of rib 6c and attachment part 6d and projected in the radially outward direction of actuator 6.

A guide groove 2 is formed in container barrel 1 between the point at which actuator 6 is positioned during use and the point at which actuator 6 is positioned after use so that actuator piece 6a of actuator 6 can be projected out from container barrel 1 through guide groove 2. In order to stably fix actuator 6 during use, a window-like in-use fixing portion 3 continuous from guide groove 2 is formed at the position where actuator 6 is to be placed during use. This in-use fixing portion 3 is formed equal in size to the length of actuator piece 6a so that actuator piece 6a is projected outwardly from container barrel 1 and has a projection 3a for preventing malfunction at the boundary with guide groove 2. This projection 3a prevents actuator piece 6a from slipping from in-use fixing portion 3 into guide groove 2 during use.

Further, in order to stably fix actuator 6 after use, a window-like after-use fixing portion 4 continuous from guide groove 2 is formed at the position where actuator 6 is to be placed after use. This after-use fixing portion 4 is formed greater in size than the length of actuator piece 6a so that actuator piece 6a is projected outwardly from container barrel 1 and is formed with a retraction projection 4a at the position corresponding to the length of actuator piece 6a. This retraction projection 4a engages actuator piece 6a when actuator piece 6a is moved back to the proximal side of container barrel 1 and fixes actuator 6 at that position.

Formed at the proximal end of container barrel 1 is a cutout portion forming a tail plug catch 5 for fixing tail plug 9. This tail plug catch 5 is a cutout of half-arrowheaded shape and a mating engaging portion 9a is formed on the tail plug 9 side.

In order to prevent outer needle 11 from being withdrawn into container barrel 1, an outer needle support lid 20 is circumferentially fitted and fixed on the distal end of container barrel 1. This outer needle support lid 20 has a gutter-like portion 20d, which is a short cylinder with a cutout portion 20c cut away from its side. In order to fix this outer needle support lid 20 to container barrel 1, this outer lid 20 further includes a fixing piece 20b to be fixed to the outer periphery at the distal end of container barrel 1 and a joint portion 20a located between fixing piece 20b and gutter-like portion 20d. The inside diameter of gutter-like portion 20d is greater than the outside dimension of attachment part 12a (FIG. 1) of inner needle 12 so as to allow attachment part 12a of inner needle 12 to be inserted but is smaller than the outside dimension of flange 11b of outer needle 11. Therefore, even when inner needle 12 is retracted into container barrel 1 by the function of the inner needle retraction mechanism, outer needle 11 will not be withdrawn into container barrel 1 because flange 11b abuts against gutter-like portion 20d.

Here, outer needle support lid 20 is fixed to container barrel 1 in such a manner that cutout portion 20c is placed in proximity to the position of actuator piece 6a of actuator 6 during use.

Referring next to FIG. 2, the operation during use will be described.

Outer needle 11 of indwelling needle body 10 together with inner needle 12 punctures the skin and reaches the vein. Then, inner needle 12 is pulled out while hub 11a of outer needle 11 being held. During this procedure, since outer needle support lid 20 has cutout portion 20c, the finger is able to hold hub 1a of outer needle 11 without any obstruction. At this point, if retraction mechanism (actuator 6 and coil spring 8) operates, outer needle 11 will not be withdrawn into container barrel 1 because there exists outer needle support lid 20 having an inside dimension smaller than the outside dimension of flange 11b of hub 11a of outer needle 11.

After inner needle 12 is pulled out, actuator piece 6a positioned at in-use fixing portion 3(FIG. 1) is moved by the finger so as to ride over projection 3a for preventing malfunction (FIG. 1) and be guided to guide groove 2. Then, coil spring 8(FIG. 1) contracts and causes actuator 6 to move to the proximal side of container barrel 1. In this movement, actuator piece 6a moves along guide groove 2 to after-use fixing portion 4(FIG. 1). Then, the actuator piece 6a now positioned at after-use fixing portion 4 is further moved back and engaged with retraction projection 4a. Thereby, actuator 6 is fixed circumferentially at that position, whereby inner needle 12 attached to actuator 6 will not erroneously come out from container barrel 1, thus making it possible to reduce the risk of occurrence of accidental needlesticks.

Since cutout portion 20c of outer needle support lid 20 is positioned in proximity to actuator 6a when it is positioned on the distal side, it is possible to perform the pulling action of inner needle 12 while holding hub 11a of outer needle 11 and the action of moving actuator piece 6a for causing retraction of inner needle 12 into container barrel 1, without changing the grip of container barrel 1.

FIG. 3 shows this indwelling needle shown in FIGS. 1 and 2, before it is used, i.e., with inner and outer needles 12 and 11 covered with a cap 13. This cap 13 has a short cylindrical portion 13a enclosing the distal part of container barrel 1. Since the indwelling needle injection device according to this embodiment is thus capped with cap 13 and is packaged and distributed, the device becomes ready for use at once by uncapping cap 13.

FIG. 4 shows the rear side of the indwelling needle shown in FIG. 3. Cap 13 has short cylindrical portion 13a enclosing the peripheral side of distal part of container barrel 1. The short cylindrical portion 13a is cut out at the position corresponding to fixing piece 20b of outer needle support lid 20, forming a fixing piece mating cutout 13b.

According to the present invention, it is possible to provide an indwelling needle which allows the inner needle to be retracted without causing retraction of the outer needle due to malfunction and will not deteriorate readiness in handling.

It is also possible to provide an indwelling needle which can be easily handled in retracting the inner needle into the device body.

What is claimed is:
1. An indwelling needle with an inner needle retraction mechanism comprising:
   the indwelling needle including a hard inner needle and a soft outer needle;
   a container barrel having distal and proximal ends, and incorporating the inner needle retraction mechanism for retracting the inner needle after use therein; and
   an outer needle support lid element fixed at the distal end of the container barrel for prohibiting the outer needle from being withdrawn into the container barrel,
   characterized in that:
      the outer needle support lid element has an external gutter-like portion;
      the gutter-like portion is a short cylinder formed in part with a cutout portion and an inside dimension thereof is designed so as to allow the inner needle to pass therethrough and be smaller than an outside dimension of a hub of the outer needle;
      the cutout portion is externally provided on the outer needle support lid element;
      the hub abuts against the gutter-like portion without being withdrawn into the gutter-like portion;
      the inner needle retraction mechanism is comprised of a guide groove formed in the container barrel in a longitudinal direction thereof, an actuator fixed to the inner needle and having an actuator piece for causing the inner needle to be retracted into the container barrel and an urging element for urging the actuator to the proximal side of the container barrel; and
      the cutout portion of the outer needle support lid element is positioned in proximity to the actuator piece.
2. The indwelling needle according to claim 1, wherein the cutout portion opens at least one end of the short cylinder.

* * * * *